US008101429B2

(12) United States Patent
Krauth et al.

(10) Patent No.: US 8,101,429 B2
(45) Date of Patent: Jan. 24, 2012

(54) NATIVE ANALYTE AS A REFERENCE IN LATERAL FLOW ASSAYS

(75) Inventors: Gary H. Krauth, Hopedale, MA (US); David J. Ledden, Medway, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 10/557,300

(22) PCT Filed: Jun. 3, 2004

(86) PCT No.: PCT/US2004/017568

§ 371 (c)(1),
(2), (4) Date: Oct. 30, 2006

(87) PCT Pub. No.: WO2004/109285

PCT Pub. Date: Dec. 16, 2004

(65) Prior Publication Data

US 2007/0172963 A1 Jul. 26, 2007

(51) Int. Cl.
*G01N 33/53* (2006.01)

(52) U.S. Cl. ........ 436/514; 436/518; 436/531; 436/533; 436/534; 436/805; 436/810; 436/808; 435/287.1; 435/287.9; 435/805; 435/810; 435/969; 435/970; 435/973; 435/975; 422/56; 422/57; 422/58; 422/59; 422/60; 422/61

(58) Field of Classification Search .................. 436/514, 436/518, 531, 533, 534, 805, 810, 808; 435/287.1, 435/287.9, 805, 810, 969, 970, 973, 975; 422/56–61

See application file for complete search history.

(56) References Cited

U.S. PATENT DOCUMENTS 4,446,232 A 5/1984 Liotta
4,943,522 A 7/1990 Eisinger et al.
5,395,754 A 3/1995 Lambotte et al.
5,451,504 A * 9/1995 Fitzpatrick et al. ............ 435/7.2

(Continued)

FOREIGN PATENT DOCUMENTS

EP 0250137 A2 12/1897

(Continued)

OTHER PUBLICATIONS

Brock et al. An Objectively Read Internal Flow Immunoassay For Urine hCG, Clinical Chemistry 49(6) Supplement (2003) F20:A151.

(Continued)

*Primary Examiner* — Bao-Thuy L Nguyen
(74) *Attorney, Agent, or Firm* — Noam R. Pollack

(57) ABSTRACT

This invention is directed to a lateral flow assay for detecting the presence of an analyte in a liquid test sample. The lateral flow assay represents an improvement in the ability to accurately and with high fidelity to detect the presence or absence of a target analyte in a liquid sample, in part, by encompassing a reference region of immobilized, non-diffusible analyte that allows for detection of any factors that interfere with the interaction and binding of the analyte to the labeled capture reagent. Any influences on the interaction and binding of the analyte that is free in solution in the liquid test sample to its complementary labeled reagent will be encountered in parallel in the binding between the immobilized analyte in reference region to the labeled reagent as it diffuses through the reference region. In one embodiment, the lateral flow assay of the invention is a urine-based human Chorionic Gonadotropin (hCG) assay.

17 Claims, 4 Drawing Sheets

Typical Test and Control Line Lateral Flow Assay with Proposed Reference Line

U.S. PATENT DOCUMENTS

| | | | | |
|---|---|---|---|---|
| 5,569,608 | A | 10/1996 | Sommer | |
| 6,183,972 | B1 | 2/2001 | Kuo et al. | |
| D456,082 | S | 4/2002 | Bouse et al. | |
| 6,436,721 | B1 | 8/2002 | Kuo et al. | |
| 6,737,278 | B1 * | 5/2004 | Carlsson et al. | 436/518 |
| 6,824,985 | B1 | 11/2004 | Rheinheimer et al. | |
| 6,924,153 | B1 * | 8/2005 | Boehringer et al. | 436/514 |
| 7,179,657 | B2 * | 2/2007 | Jerome et al. | 436/514 |
| 2001/0019829 | A1 * | 9/2001 | Nelson et al. | 435/7.1 |
| 2002/0146844 | A1 | 10/2002 | Pronovost et al. | |

FOREIGN PATENT DOCUMENTS

| | | | |
|---|---|---|---|
| EP | 0253464 | A1 | 1/1988 |
| EP | 0462376 | A2 | 12/1991 |
| EP | 0724157 | A2 | 7/1996 |
| FR | 2788856 | | 7/2000 |
| JP | 11-113023 | | 5/1999 |
| JP | 2000-097944 | | 7/2000 |
| WO | WO 88/08534 | * | 11/1988 |
| WO | WO9638720 | | 12/1996 |
| WO | WO9709620 | | 3/1997 |
| WO | WO9936777 | | 7/1999 |
| WO | WO0029852 | | 5/2000 |
| WO | WO0043786 | | 7/2000 |

OTHER PUBLICATIONS

International Search Report of International Application No. PCT/US2004/017568 mailed Oct. 14, 2004.

Written Opinion of International Application No. PCT/US2004/017568 mailed Oct. 12, 2004.

Butler et al., "Detection of Early Pregnancy Forms of Human Chorionic Gonadotropin by Home Pregnancy Test Devices", 2001, Clinical Chemistry 47:12, pp. 2131-2136.

"SureStep hCG Combo Pregnancy Test", ABI Applied Biotech, Inc.-Diagnostic Products, pp. 1-2.

"SureStep hCG Combo (II) Pregnancy Test with Reference Line", Sep. 2002, Applied Biotech, Inc., pp. 1-2.

* cited by examiner

NATIVE ANALYTE AS A REFERENCE IN LATERAL FLOW ASSAYS

BACKGROUND OF THE INVENTION

The invention relates to determining the concentration of analyte in a liquid test sample by immunochromatography techniques.

Immunochromatographic strip formats have become increasingly popular for qualitative, semi-quantitative and quantitative assays that use visual detection schemes. This type of immunoassay involves the application of a liquid test sample suspected of containing an analyte to be detected to an application zone of an immunochromatographic test strip. The strip includes a matrix material through which the liquid test medium and analyte suspended or dissolved therein can flow by capillarity from the application zone to a capture zone where a detectable signal, or the absence of such, reveals the presence of the analyte. Typically, the strip includes a means for immunospecifically binding the analyte to be detected with its specific binding partner that bears the detectable label. In one such scheme, as disclosed in U.S. Pat. No. 4,446,232, the strip contains an enzyme labeled, mobile binding partner for the analyte which is in a zone of the strip downstream from the sample application zone. If analyte is present in the test sample, it combines with its labeled binding partner to form a complex that flows along the strip to a detection zone containing a substrate for the enzyme label capable of providing a colored response in the presence of the enzyme label. The strip contains another zone in which analyte is immobilized, so that the labeled binding partner which does not combine with analyte, due to the absence of sufficient analyte in the sample, is captured and thereby inhibited from reaching the detection zone. There have been published various modifications of this technique, all of which involve competitive specific binding systems in which the presence or absence of analyte in the test sample is determined by the detection or lack thereof of labeled binding partner in the capture zone.

In European patent application EP 0 462 376 there is disclosed a procedure in which signal at the capture site and conjugate collection site of an immunochromatographic strip are detected and the analyte concentration is determined by the intensity of the signal at the capture site relative to the signal at the recovery site. Also of interest in this regard is U.S. Pat. Nos. 5,569,608, 6,183,972 and 6,436,721, each of which is incorporated herein by reference.

Most lateral flow immunochemical tests are also provided with a procedural control that typically consists of an anti-species antibody (to the antibody attached to the colored particle) bound to the membrane distal to the test line. Appearance of a colored line confirms that the correct procedures were used. Thus, it confirms that sample was added, it mixed with and solubilized the colored particle dried to the pad and the complex flowed through the membrane resulting in binding of the colored particle to the control line. The sample then continues to move up the strip to the control band that contains an immobile band of anti-species IgG to produce the control line.

Some manufacturers also provide a reference line that is located midway between the test and control lines. See, SureStep™ hCG Combo (II) Pregnancy Test, Product Insert, Catalog #6018, Applied Biotech, Inc., San Diego, Calif. The reference line is made by applying a fixed concentration of another nonspecific immunoglobin to the membrane midway between the test and control line. To the pad, which contains the human chorionic gonadotropin (hCG) antibody attached to a colored particle, is added another colored particle to which an antibody to the reference immunoglobin is attached. The amount of nonspecific immunoglobin and concentration of colored particle is adjusted to result in a reference line having an intensity equivalent to that of the test line's sensitivity claim for pregnancy detection. Thus, a test line's intensity equal to or greater than the reference line intensity would be indicative of pregnancy.

However, unlike serum samples, whose compositions are typically very consistent in terms of, for example, pH, protein concentration and ionic strength, urine samples are considerably more variable in composition. These differences represent interfering factors that can impact the immunochemical binding and influence the accuracy of the result. Many manufacturers formulate their tests to compensate for some of these sample differences, for example, pH and protein levels, by drying the colored particle in a buffer containing protein. However, additional interfering factors exist, for example, urine specific gravity (SG), which impact the accuracy of lateral flow immunochemical tests by interfering with binding of the analyte to its complementary binding reagent. Comparison of test line intensity to reference line intensity is of little value unless the immunochemical reagents for the reference line are identical to those for the test line and are impacted, to the same degree, by variations in interfering factors such as specific gravity.

Thus, there exists a need for a reference reagent system similar to that utilized for the test reagent system such that interferences in immunochemical binding show parallel effects on both systems. Ideally, the intensity of signal observed in the reference region intensity would parallel that of the test region so as to ensure greater fidelity of the result. The present invention satisfies this need and provides related advantages as well.

SUMMARY OF THE INVENTION

The invention is directed to a lateral flow assay that encompasses a first region that contains a diffusibly bound labeled reagent complementary to a target analyte in the liquid sample, wherein the diffusibly bound labeled reagent and the target analyte form a diffusible first complex; a test region that contains a non-diffusibly bound capture reagent capable of complexing with the first complex; a control region that contains a non-diffusibly bound control reagent that is complementary to the diffusively bound labeled reagent; and a reference region that contains a non-diffusibly bound analyte capable of complexing with the diffusibly bound labeled reagent.

The invention provides a lateral flow assay for detecting the presence of an analyte in a liquid test sample, for example, a urine sample. The lateral flow assay represents an improvement in the ability to accurately and with high fidelity to detect the presence or absence of a target analyte in a liquid sample, in part, by encompassing a reference region of immobilized, non-diffusible analyte that allows for detection of any factors that interfere with the interaction and binding of the analyte to the labeled capture reagent. Any influences on the interaction and binding of the analyte that is free in solution in the liquid test sample to its complementary labeled reagent will be encountered in parallel in the binding between the immobilized analyte in reference region to the labeled reagent as it diffuses through the reference region.

DETAILED DESCRIPTION OF THE INVENTION

Figure 1:
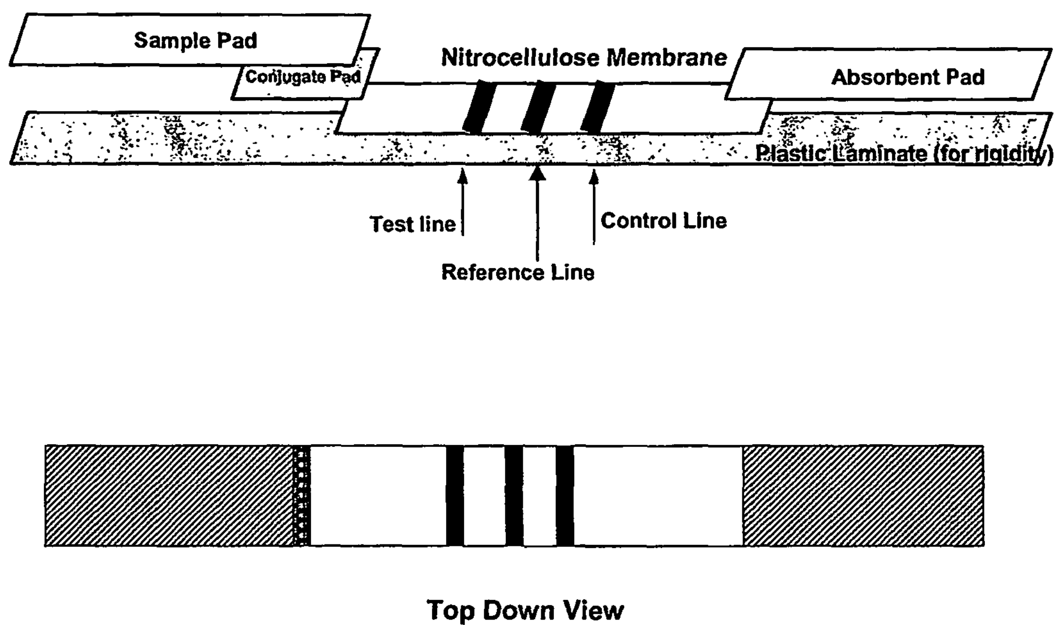
FIG. 1 shows a diagram that depicts the configuration matrix configuration in one embodiment of a lateral flow assay of the invention. In this embodiment, the reference region containing the non-diffusibly bound analyte is located between the test and control regions.

This invention is directed to a lateral flow assay for detecting the presence of an analyte in a liquid sample. The lateral flow assay represents an improvement in the ability to accurately and with high fidelity to detect the presence or absence of a target analyte in a liquid sample, in part, by encompassing a reference region of immobilized, non-diffusible analyte that allows for detection of any factors that interfere with the interaction and binding of the analyte to the labeled capture reagent. Any influences on the interaction and binding of the analyte that is free in solution in the liquid test sample to its complementary labeled reagent will be encountered in parallel in the binding between the immobilized analyte in reference region to the labeled reagent as it diffuses through the reference region.

In one embodiment, the lateral flow assay of the invention is a urine-based assay. Unlike serum samples, urine samples show variation in their composition due to a variety of factors including, for example, pH, protein content and ionic strength. These and other factors represent interferants that can influence the interaction between an analyte contained in the urine and a binding partner complementary to the particular analyte. While some of these interferants can be accounted for by taking particular measures in how an assay is designed, other interfering factors, for example, differences in specific gravity (SG) of urine, will impact the accuracy of a lateral flow assay.

The lateral flow assay provided by the invention encompasses a first region that contains a diffusibly bound labeled reagent complementary to a target analyte in the liquid sample, wherein the diffusibly bound labeled reagent and the target analyte form a diffusible first complex; a test region that contains a non-diffusibly bound capture reagent capable of complexing with the first complex; a control region that contains a non-diffusibly bound control reagent that is complementary to the diffusively bound labeled reagent; and a reference region that contains a non-diffusibly bound analyte capable of complexing with the diffusibly bound labeled reagent. As described in more detail below, the relative position of the reference region vis-à-vis the first, test and control regions can be selected based on a variety of factors taken into account by the skilled person. In particular, the reference region can be located either between the first region and the test region or, alternatively, can be located between the test region and the control region.

The lateral flow assay provided by the invention can be a urine-based immunochemical test that provides a reference region of non-diffusibly bound analyte that allows for the detection of interfering factors that affect binding of any analyte contained in a liquid sample to the complementary labeled reagent. While some of the mobilized first complex formed by the labeled reagent bound to the target analyte will complex with the capture reagent in the test region, excess mobilized labeled reagent will bind to and complex with the non-diffusibly bound analyte in the reference region. Any interfering factors, also referred to herein as "interferants", associated with the particular liquid sample that affect the binding of analyte to the complementary labeled reagent will affect the test region and reference region in parallel. Thus, the invention provides a reference region that is subject to and proportionally affected by the same interfering factors as the test region.

The term "target analyte" as used herein refers to a compound or composition to be detected or measured in the test sample. The target analyte will have at least one epitope that an antibody or an immunological reactive fragment thereof can recognize. A target analyte can be any antigenic substance, hapten, antibody and combination thereof. The analyte of interest in an assay can be, for example, a protein, a peptide, an amino acid, a nucleic acid, a hormone, a steroid, a vitamin, a pathogenic microorganism for which polyclonal and/or monoclonal antibodies can be produced, a natural or synthetic chemical substance, a contaminant, a drug including those administered for therapeutic purposes as well as those administered for illicit purposes, and metabolites of or antibodies to any of the above substances. A preferred example of a hormone suitable for detection is human Chorionic Gonadotropin (hCG). The lateral flow assay provided by the invention can test for the presence of a variety of target analytes, for example, of Follicular Stimulating Hormone (FSH), Luteinizing Hormone (LH), gonorrhea antigen, Chlamydia antigen, Cross linked N-telopeptides, Deoxyprydinolone (Dpd), HIV antibodies and Nuclear Membrane Protein-22 (NMP-22).

Suitable target analytes to which the method of the invention can be applied are any for which a specific binding partner can be found. In general, most target analytes of medical and biological significance can find specific binding partners in antibodies prepared against them or fragments of these antibodies. Suitable target analytes thus include any soluble analytes such as hormones, enzymes, lipoproteins, bacterial or viral antigens, immunoglobulins, lymphokines, cytokines, drugs, soluble cancer antigens, and the like. These analytes include various proteins such as protamines, histones, porphorylated proteins, nucleoproteins, and so forth such as, for example, transcortin, erythropoietin, transferrin, various globulins, thyroxin-binding globulin, the immunoglobulins of various subclasses A, G, D, E, and M, various complement factors, blood clotting factors such as fibrinogen, Factor VIII, tissue thromboplastin, and thrombin.

Also included are analytes that can be targeted are hormones such as insulin, glucagon, relaxin, thyrotropin, somatotropin, gonadotropin, gastin, bradykinin, vasopressin, and various releasing factors. A wide range or antigenic polysaccharides can also be determined such as those from *Chlamydia, Neisseria gonorrheae, Pasteurella Destis, Shigella dysentereae*, and certain fungi such as *Mycosporum* and *Aspergillus*. Another major group of suitable target analytes comprises oligonucleotide sequences which react specifically with other oligonucleotides or protein targets.

In the embodiments of the invention, it is essential that the labeled reagent migrates with the liquid sample as it mobilizes by diffusion through the matrix of the assay. The lateral flow assay thus contains a matrix through which the fluid sample can flow by capillarity.

As used herein, the term "matrix" refers to any porous material capable of providing lateral flow. This includes material such as nitrocellulose, nitrocellulose blends with polyester or cellulose, untreated paper, porous paper, rayon, glass fiber, acrylonitrile copolymer or nylon. One skilled in the art will be aware of other porous materials useful in a matrix of the invention that allow lateral flow. Typically, the matrix will be in the form of a strip through which the test fluid flows horizontally although the matrix could be set up in layers through which the test fluid could flow vertically from top to bottom or vice-versa.

The strip can be prepared from any matrix material through which the test fluid and an analyte contained therein can flow by capillarity. The matrix can be of a material which is capable of non-bibulous lateral flow. Typically, the chromatographic matrix comprises a solid phase that is can be rectangular in shape such that the liquid sample can be applied at or near the first end of the solid phase of the chromatographic matrix and diffuse by capillary action through the matrix. This type of flow is described in U.S. Pat. No. 4,943,522 as liquid flow in which all of the dissolved or dispersed components of the liquid are carried through the matrix at substantially equal rates and with relatively unimpaired flow, as opposed to preferential retention of one or more components as would be the case if the matrix material were capable of adsorbing or imbibing one or more of the components. An example of such a matrix material is the high density or ultra high molecular weight polyethylene sheet material or any other absorbent or porous material suitable as a medium for thin layer chromatography of analyte and analyte-antibody conjugates, such as nitrocellulose, nylon, rayon, cellulose, paper, silica or non-woven or porous synthetic materials. The chromatographic matrix can be pretreated or modified as needed. The chromatographic matrix can be translucent, so that signal appearing on it can be viewed from either side.

The term "lateral flow" refers to liquid flow by capillarity in which all of the dissolved of dispersed components of the liquid are carried at substantially equal rates and with relatively unimpaired flow laterally through a matrix, as opposed to preferential retention of one or more components as would occur with matrices capable of adsorbing or imbibing one or more components.

The term "diffusibly bound" as referred to herein means that a reagent is attached, or impregnated, but capable of dispersing with the liquid sample and being carried by the liquid sample in the lateral flow. The term "non-diffusibly bound" as used herein refers to reagents which are attached to the support such that lateral flow of the liquid sample does not affect the placement of the immobile reagent in the discrete region of the matrix. Such attachment can be through covalent or ionic means. Those skilled in the art will be aware of means of attachment to non-diffusibly bind various reagents.

The term "labeled reagent" as used herein refers to any particle, protein or molecule which recognizes or binds to the target analyte in question and has attached conjugated or bound to it, either chemically, covalently or noncovalently, ionicly or nonionicly any substance capable of producing a signal that is detectable by visual or instrumental means. The labeled reagent is diffusibly bound to the matrix in the first region of the lateral flow assay of the invention. The reagent has attached to it a label component that is capable of producing a signal. Suitable label components of the labeled reagent include chromogens, catalysts, fluorescent compounds, colloidal metallic and nonmetallic particles, dye particles, enzymes or substrates, organic polymers, latex particles, liposomes with signal producing substances and the like. The reagent component of the labeled reagent can be a particle or molecule capable of recognizing the analyte and can be either natural or non-natural, preferably a monoclonal or polyclonal antibody or fragment thereof. In one embodiment of the invention, the labeled reagent can be a monoclonal antibody to hCG or to the β-epitope of hCG bound to gold sol or dyed polystyrene microbeads.

The term "sample" as used herein refers to any biological sample that could contain an analyte for detection. Preferably the biological sample is in liquid form or can be changed into a liquid form. Preferably, the sample is a urine sample.

The term "capture reagent" as used herein refers to any particle or molecule which recognizes or binds the target analyte in question. The capture reagent is capable of forming a binding complex with the first complex formed by the labeled reagent and analyte in the sample. The capture reagent is non-diffusibly bound to the porous material that makes up the test region of matrix of the lateral flow assay. The capture reagent is not mobilized by the lateral flow of the liquid sample due to the being non-diffusibly bound to the porous matrix material. The capture reagent can be a natural or non-natural, in particular, synthetic molecule. Once the first complex has diffused with the lateral flow of the liquid sample to the test region where the capture reagent is non-diffusibly bound, the capture reagent binds the first complex consisting labeled reagent and analyte. In one embodiment of the invention, the labeled reagent can be a monoclonal antibody to intact hCG that recognized an epitope distinct from that recognized by the labeled reagent.

As described herein, the lateral flow assay of the invention includes a reference region that comprises non-diffusibly bound native analyte. Presence of the reference region allows for detection of interference in binding between the analyte that is free in solution in the liquid sample and the diffusibly-bound labeled reagent that is immobilized in the first region of the matrix. By containing non-diffusibly bound native analyte, the reference region serves as an indirect indicator of the presence of any interferants that affect binding of analyte to labeled reagent. In particular, because the reagent systems are the same, the signal intensities between the test region and the reference region parallel each other as a function of interference that is encountered in binding between the analyte and its complementary reagent. As described herein, high SG of a urine sample similarly influences binding to labeled reagent of both the analyte free in solution in the urine sample as it penetrates the first region and the non-diffusibly bound analyte present in the reference region.

The concentration of the non-diffusibly bound analyte in the reference region can be distributed in the reference region at a predetermined concentration desired by the user. For example, the analyte can be distributed at the minimum or cut-off concentration of analyte for which a signal is still readily detectable either by visual or instrumental means. In this embodiment of the invention, the signal can be determined either by visual or by instrumental means. In the absence of any interferences in binding between the analyte and its complementary labeled reagent, a signal can be expected in the reference region upon binding between the labeled reagent as it mobilizes through the reference region and binds the non-diffusibly bound analyte present in that region. Conversely, the absence of a signal detected as a result of the labeled reagent mobilizing through the reference region and binding the non-diffusibly bound analyte would indicate the presence of factors that interfere with the binding. The ability to ascertain the presence of factors that interfere with binding is significant in the absence of a positive signal in the test region, where the same interfering factors would be expected to result in a parallel impact on signal strength. In particular, the absence of a signal in both the reference region and test region alerts the user to the possibility that a false negative result may have been obtained and confirmatory testing is warranted to ensure accuracy of the result.

In addition to being distributed at a minimum or cut-off concentration, the non-diffusibly bound native analyte also can be distributed at a concentration that is predetermined to produce a particular reflectance signal. In this embodiment of the invention the ratio of the expected signal and the observed signal can be used to determine the presence of factors that interfere with binding. A higher the ratio of expected signal over observed signal, increases the likelihood that a factor is present that interferes with the binding of the analyte and its complementary reagent.

Thus, the invention provides a lateral flow assay that contains a reference region of non-diffusibly bound analyte at a concentration that represents the minimum concentration at which the presence of the analyte can be detected visually and without instrumentation. In a related embodiment, the invention provides a lateral flow assay that contains a reference region of non-diffusibly bound analyte at a concentration that represents the minimum concentration at which the presence of the analyte can be detected by an instrument having a detector capable of measuring the signal from the detectable label. The concentration of the analyte in the reference region can be predetermined such that a signal detected in the reference region indicates that the assay is sensitive to the analyte at minimum detectable concentration. As described herein, the absence of signal in both of the reference region and the test region in combination with presence of signal in the control region can indicate the likelihood of a false negative result.

The position of the reference region vis-à-vis the first, test and control regions can be selected to be located either between the first region and the test region or, alternatively, between the test region and the control region. Selection of the relative position of the reference region can be based on a variety of factors, for example, the test response to high analyte concentration in the sample. In particular, if high analyte concentrations result in a significant proportion of the first complex binding to the capture reagent, the reference region can be positioned such that the first complex contacts it prior to contacting the test region. Conversely, if high analyte concentrations do not result in a significant proportion of the first complex binding to the capture reagent in the test region, the reference region can be positioned between the test region and the control region.

Figure 4:
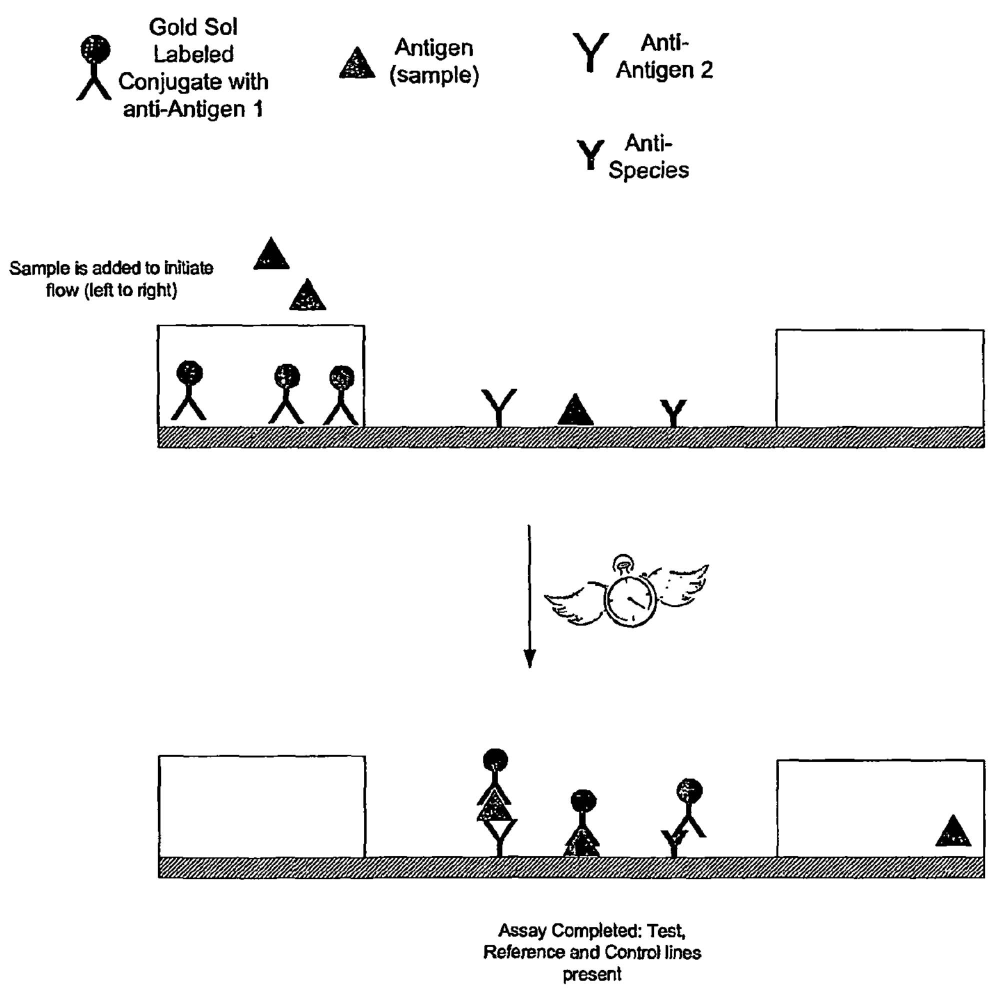
FIG. 4 shows a schematic of a lateral flow assay that contains a reference region of non-diffusibly bound analyte.

In a particular embodiment, the invention provides a lateral flow assay for detecting the presence of hCG in a urine sample, wherein the assay contains a first region comprising a diffusibly bound labeled anti-hCG antibody, wherein the diffusibly bound labeled anti-hCG antibody and hCG form a diffusible first complex; a test region containing a non diffusibly bound antibody to intact hCG capable of complexing with the first complex; a control region comprising a non-diffusibly bound control antibody that is an anti-species antibody to the diffusibly bound labeled antibody of the first region; and a reference region comprising non-diffusibly bound hCG capable of complexing with said diffusibly bound labeled anti-hCG antibody. A schematic depicting a lateral test assay of the invention is provided in FIG. 4.

As used herein, the term "control region" refers to a region that confirms to the user that the assay has worked as designed. In a lateral flow assay of the invention, the term is used for the zone that confirms that the liquid sample has permeated or flowed through the matrix as designed. For example, the control region can contain a non-diffusibly bound control reagent that is complementary to the diffusively bound labeled reagent of the first region. Thus, the control region can contain a non-diffusibly bound binding partner, for example, and anti-species antibody that will bind to the labeled antibody from the first region, such as an anti-mouse antibody if the labeled reagent has been derived from a murine hybridoma.

Alternatively, the control region can contain an anhydrous reagent that, when moistened, produces a color change or color formation, for example, anhydrous copper sulphate which will turn blue when moistened by an aqueous sample. In order to effectively confirm that the test has been completed, the control region should be located downstream from the test region in which the test result is recorded. A positive signal in the control region informs the user that the sample has permeated the required distance through the lateral flow assay matrix.

The term "control reagent" as used herein refers to any particle or molecule which is capable of binding the labeling reagent and which does not recognize or bind the analyte in the sample. For example, the labeled capture reagent may be an antibody specific to the analyte conjugated to a gold sol. In this embodiment, the control reagent can be an anti-species antibody to the to the labeled capture reagent. Thus, the control reagent can be a monoclonal or polyclonal antibody which recognizes the labeled reagent. The control reagent is non-diffusibly bound to matrix in the control region, which is located downstream of the test region. The control reagent binds and immobilizes the labeled capture reagent. Just as the labeled reagent is non-diffusibly bound at a discrete situs on the matrix, the control reagent is also immobilized in a discrete situs on the matrix referred to as the control region.

By measuring the signal from the physically detectable property of the detectable label in the reference zone containing the immobilized analyte as the binding means and the signal from the physically detectable property of the label in the test zone, in which the immobilized capture reagent against the labeled first complex is the binding means, and determining the ratio of these signals, the accuracy of the test for analyte can be increased. The accuracy is increased because this technique corrects for interfering factors that disturb the binding interaction between analyte and reagent.

The label can be an entity the presence of which can be readily detected. Preferably the label is a direct label which, in its natural state, is readily visible either to the naked eye, or with the aid of an optical filter and/or applied stimulation, for example UV light to promote fluorescence. For example, minute colored particles, such as dye sols, metallic sols (in particular, gold), and colored latex particles are suitable labels for a reagent of the invention. Concentration of the label into a small region or volume should give rise to a readily detectable signal that can be evaluated by visually, or by instrumentation if desired.

Indirect labels, such as enzymes, for example, alkaline phosphatase and horseradish peroxidase, can be used but these usually require the addition of one or more developing reagents such as substrates before a visible signal can be detected. If necessary, such additional reagents can be incorporated in the matrix such that they dissolve or disperse in the aqueous liquid sample. Alternatively, the developing reagents can be added to the sample before contact with the lateral flow assay such that the signal is exposed to the developing reagents after the binding reaction has taken place.

Coupling of the label to the reagent can be by covalent bonding, if desired, or by hydrophobic bonding. Such techniques are commonly practiced by those skilled in the art. In embodiments where the label is a direct label such as a gold sol or colored latex particle, hydrophobic bonding is preferred.

As described herein, the lateral flow assay provided by the invention is a immunochemical test that provides a reference region of non-diffusibly bound analyte that allows for the detection of interfering factors that affect binding of analyte contained in a liquid sample to the complementary labeled reagent. In one embodiment, the lateral flow assay provided by the invention is a urine-based immunochemical test. For a urine-based lateral flow assay, interfering factors include, for example, the specific gravity (SG) of the urine, pH, total protein, urea or glucosuria These factors interfere with immunochemical binding and, hence, influence the accuracy of the result. While some interferants can be compensated for by, for example, drying the colored particle in a buffer containing protein, which helps to minimize differences in pH and protein levels between various samples, other interferants, for example, urine specific gravity (SG), which typically result from diurnal variations in the composition and concentration of various salts as well as urea, will impact of the accuracy of lateral flow immunochemical tests. The lateral flow assay of the invention can incorporate any compensatory measures known in the art that are directed to minimizing the influence of interferants.

Figure 2:
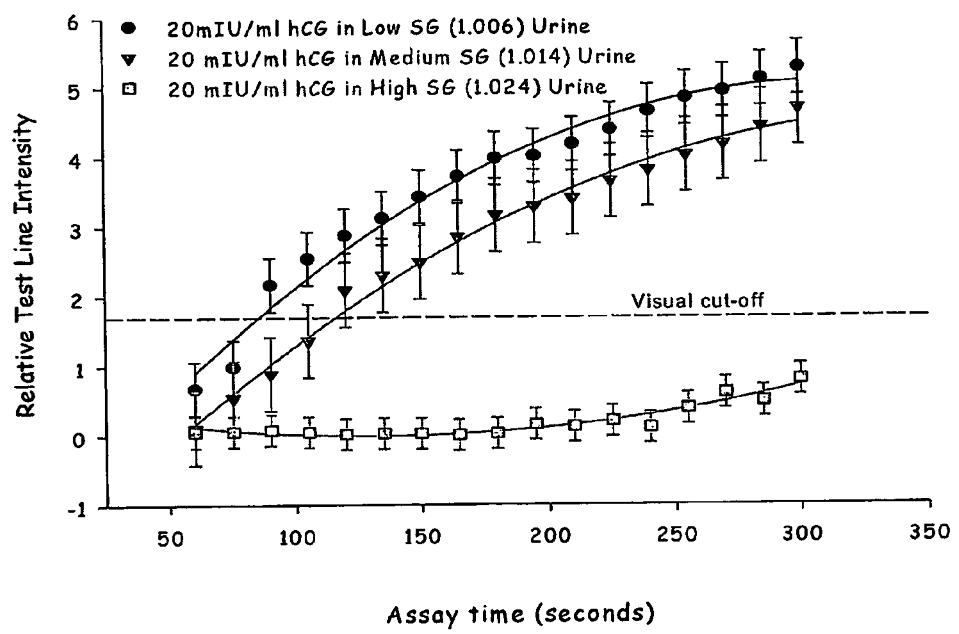
FIG. 2 shows the kinetic response for an hCG sample in urine having three different Specific Gravities.

With regard to specific gravity (SG), FIG. 2 shows the kinetic response for a 20 mLU/ml hCG sample in urine having three different SGs. As shown in FIG. 2, the relative test line intensity is inversely proportional to the sample SG. In contrast to a moderately high SG (1.024) sample, which is not visually detectable, the test line intensities for low and medium SG samples can be visually detectable as early as 120 seconds after sample addition. Normally, SG varies between 1.010 and 1.025 (Mean 1.015) and is typically highest in the first morning void. Therefore, test accuracy can be compromised particularly for samples encompassing a first morning void and containing relatively low levels of hCG. Comparison of test line intensity to control line intensity is of limited value, however, since the immunochemical reagents for the control line are different than those for the test line and are not impacted, to the same degree, by variations in SG. The present invention provides a solution to this problem by providing a reference region that produces a reference line intensity that is subject to the same interfering factors as the test line intensity.

Thus, the present invention relates to the use of native analyte, for example, native hCG as the reference line material because influences on binding between the analyte contained in the liquid sample solution, would similarly affect binding of the labeled reagent to the bound native analyte in the reference region because the two reagent systems are the same. While some of the first complex will bind to the test line, and in proportion to the amount of analyte in the sample, there is still sufficient labeled reagent remaining to bind to the low level hCG-containing reference line. This is because the manufacturer typically provides a large excess of labeled capture reagent to help speed up the reaction and to minimize issues associated with the so-called high-dose hook effect, where less binding is experienced in the presence of very high concentrations of analyte.

In a particular embodiment of the present invention, there is provided a reflectance spectrometer with means for moving the strip or detector relative to each other such as a specimen table on which the strip is placed which can be moved laterally under the read head of the detector. In the case of the detectable physical property being reflectance of light at a predetermined wavelength, the detector is a spectrometer. This technique will assist in providing accurate quantitation for regions of the strip which may not have been precisely located with respect to the detection means of the spectrometer. More specifically, the location of the strip relative to the detector can be under microprocessor control, so that the reflectance of any desired region can be determined. Thus, the invention provides a lateral flow assay that is read by a reflectance spectrometer, for example, Bayer Diagnostics' CLINITEK Status®. The reading can be provided by the instrument as a K/S value derived from the reflectance measured.

As described herein, signal intensities in a lateral flow assay of the invention can be detected and evaluated visually or by instrumentation. For instrument detection of hCG in a liquid sample, a reflectance-based desktop analyzer utilizing a touch screen for the primary user-interface, for example, Bayer Diagnostics' CLINITEK Status® system adapted for hCG and called Clinitest® hCG can be utilized as described in Brock et al., *Clinical Chemistry* 49(6) Supplement, 2003, A151 (F20). A reflectance-based analyzer can read a variety of lateral flow immunoassays in both strip and plastic cassette formats as well as existing urine chemistries, for example, Bayer Diagnostics' Multistix®, which is equipped with a motor driven table that contains a reversible insert for aligning strip or cassette-based tests. A dosed urine chemistry strip or lateral flow assay can be placed on a table that automatically determines the test identification and the associated read time required for optimal performance and the hCG results can be reported as "negative" (for example, less than 2 mIU/ml) or "positive" (for example, greater than 25 mIU/ml) with results in between noted as "borderline retest in 48-72 hours". Final test results can be communicated both through the touch screen and by hard copy with the on-board printer that uses either continuous feed paper or label stock. Instrument detection with a reflectance meter, for example, Bayer Diagnostics' CLINITEK Status®, can eliminate inter and intra-reader variability due to, for example, differences in visual acuity and/or ambient lighting.

It is understood that modifications which do not substantially affect the activity of the various embodiments of this invention are also included within the definition of the invention provided herein. Accordingly, the following examples are intended to illustrate but not limit the present invention.

EXAMPLE I

Qualitative Detection of hCG in Urine Using a Reference Line to Correct for Potential Interferences This Example demonstrates the qualitative detection of hCG using a reference line containing immobilized hCG that allows for correction of potential inferences with the binding of free in solution hCG in the sample and labeled monoclonal anti-beta hCG antibody.

An immunochemical strip containing a sample pad (sample application, sample treatment and filtration), conjugate pad (containing gold sol labeled monoclonal anti-beta hCG antibody), nitrocellulose membrane (test line is goat anti-hCG antibody, reference line is hCG and control line which is goat anti-mouse IgG) and an absorbent pad. This strip is illustrated in FIG. 1.

Preparation of Reagent Cards

Reagent cards are prepared by assembling the various subcomponents onto an adhesive plastic laminate and then cutting reagent strips of various widths for use in either a dipstick format or cassette-based format. An example of a dipstick format is Applied Biotech, Inc's. SureStrip™ hCG Pregnancy Test, Catalog #6007, which is a strip 5 mm wide. The Clinitest® hCG Pregnancy Test, also manufactured by Applied Biotech, Inc., contains an 8 mm wide test strip encased in a plastic cassette (Bayer Corporation, US D456,082S).

Application of Critical Reagents

The conjugate pad (7 mm long) is saturated with a 1:10 dilution of a solution containing 0.048 mg mouse anti-hCG (in phosphate buffered saline, pH 7.4)/mL gold sol solution (absorbance at 520 nm of 4.0 for 40 nm diameter particles)

and dried. Goat anti-hCG (1.5 mg/mL phosphate buffered saline, pH 7.4) is striped on nitrocellulose at the Test line location. For the reference region, purified hCG (in phosphate buffered saline, pH 7.4), is striped at a concentration that would result in a reference line intensity equivalent to the application of 200 uL of a 25 mIU/mL hCG test solution. Furthermore, 2.0 mg/mL of goat anti-mouse IgG, in phosphate buffered saline, pH 7.4, is striped in the control region. The prepared matrix is subsequently dried.

The test device is then assembled by first centering and fixing the striped and dried membrane matrix (25 mm long) on a 60 mm long by 25 cm wide plastic laminate. The dried conjugate pad is added such that 0.5 mm of the conjugate pad contacts the matrix consisting of nitrocellulose membrane. The sample pad (20 mm long) is subsequently fixed over the conjugate pad exposing 0.5 mm of the later pad. Finally, the absorbent pad (16 mm long) is fixed at the opposite end of the strip. The assembled card can now be cut into either 5 mm wide strips, for use in a dipstick format, or in 8 mm wide strips for use in cassettes.

Dipstick Format

To evaluate the effect of specific gravity on the binding kinetics of hCG, a stock hCG solution was spiked into pooled male urine to produce a test solution of 20 mIU/mL hCG in low (1.006), medium (1.014) and high (1.024) specific gravity urine. Assembled 5 mm wide strips (replicates of five) were dipped (dipstick format) into the urine samples for 15 seconds, at room temperature, and resulting peak amplitudes (relative intensity) measured and recorded every 15 seconds over a 5-minute assay development time on the Clinitek Status® instrument. Results are shown in FIG. 2.

Cassette Format

To confirm the specific gravity impact on Test line binding intensity, twenty-seven male and 11 non-pregnant female urine samples were spiked with a stock hCG solution to produce samples containing 25 mIU/mL hCG. Individual urine specific gravity measurements were made with a TS meter. Briefly, 200 uL of spiked urine was added to the cassette test, the device put into the Clinitek Status® instrument which automatically reads the Test line intensity 5 minutes after dosing. Each sample was assayed on three different Clinitek Status® instruments on each of two reagent card lots. Results of this combined (male and female spiked urine samples) study are shown in FIG. 3 with error bars depicting the 95% confidence interval.

Figure 3:
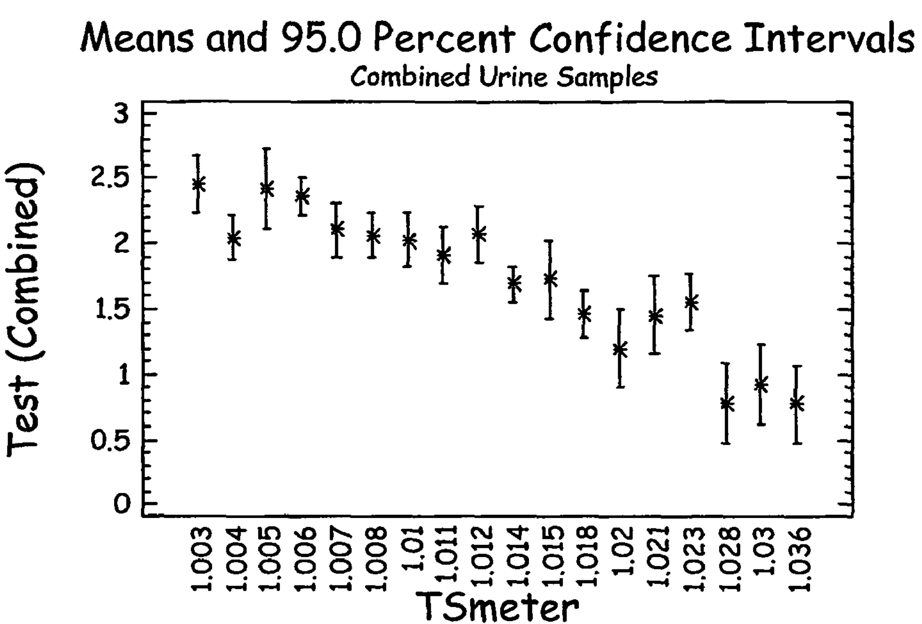
FIG. 3 shows how test line intensity decreases as a function of specific gravity.

As shown FIG. 3, the Test line intensity decreases as a function of specific gravity. With hCG striped at the Reference region, however, the relative binding intensity of the Reference line parallels that of the Test line, producing a constant ratio as a function of specific gravity and allowing for correction of differences in specific gravity.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

We claim:

1. A lateral flow sandwich assay device for detecting the presence of an analyte in a liquid sample, said assay device comprising: (a) a first region comprising a diffusibly bound labeled reagent complementary to an analyte in the liquid sample, wherein said diffusibly bound labeled reagent and said analyte form a diffusible first complex; (b) a test region comprising a non-diffusibly bound capture reagent capable of complexing with the first complex such that said analyte is bound between said non-diffusibly bound capture reagent and said diffusibly bound labeled reagent; (c) a control region comprising a non-diffusibly bound control reagent complementary to the diffusively bound labeled reagent and (d) a reference region comprising a predetermined concentration of non-diffusibly bound analyte that will complex with said diffusibly bound labeled reagent upon operation of the device to form a complex having a predetermined signal intensity, said non-diffusibly bound analyte having substantially the same affinity for said diffusibly bound labeled reagent as said diffusibly bound labeled reagent has for said analyte in the liquid sample such that any influences on the interaction and binding of analyte and diffusibly bound labeled reagent in said first region would be similarly encountered in the interaction and binding of said non-diffusibly bound analyte with said diffusibly bound labeled reagent in said reference region such that said predetermined signal intensity can serve as a_reference to indicate, by a comparison of the actual signal intensity of said reference region to said predetermined signal intensity, the presence of interferants that negatively impact the interaction and binding of analyte and diffusibly bound labeled reagent in said first region.

2. The lateral flow sandwich assay device of claim 1, further comprising a matrix through which the liquid sample can flow by capillarity.

3. The lateral flow sandwich assay device of claim 2, wherein said matrix comprises nitrocellulose.

4. The lateral flow sandwich assay device of claim 1, wherein said diffusibly bound labeled reagent is complementary to an analyte selected from the group consisting of Follicular Stimulating Hormone (FSH), human Chorionic Gonadotropin (hCG), Luteinizing Hormone (LH), Gonorrhea antigen, Chlamydia antigen, Cross linked N-telopeptides, Deoxyprydinolone (Dpd), HIV antibodies and Nuclear Membrane Protein-22 (NMP-22).

5. The lateral flow sandwich assay device of claim 4, wherein said analyte is human Chorionic Gonadotrophin (hCG).

6. The lateral flow sandwich assay device of claim 4, wherein said analyte is Luteinizing Hormone (LH).

7. The lateral flow sandwich assay device of claim 1, wherein said reference region is located between said first region and said test region.

8. The lateral flow sandwich assay device of claim 1, wherein said reference region is located in between said test region and said control region.

9. The lateral flow sandwich assay device of claim 1, wherein said diffusibly bound labeled reagent comprises an antibody.

10. The lateral flow sandwich assay device of claim 1, wherein said diffusibly bound labeled reagent comprises an anti-hCG antibody capable of specifically binding with hCG to form a first complex of said labeled anti-hCG antibody and said hCG.

11. The lateral flow sandwich assay device of claim 1, wherein said label is a gold sol.

12. The lateral flow sandwich assay device of claim 1, wherein said label is colored latex particles.

13. The lateral flow sandwich assay device of claim 1, wherein said predetermined concentration represents the minimum concentration at which the presence of the analyte can be detected visually and without instrumentation.

14. The lateral flow sandwich assay device of claim 1, wherein said predetermined concentration represents the minimum concentration at which the presence of the analyte can be detected by an instrument having a detector capable of measuring the signal from the detectable label.

15. The lateral flow sandwich assay device of claim 1, wherein said predetermined concentration is selected such that its predetermined signal intensity can be used to as a reference to indicate the presence of interferants that negatively impact the interaction and binding of analyte and diffusibly bound labeled reagent in said first region such that a signal detected in the reference region indicates that the assay is sensitive to the analyte at minimum detectable concentration.

16. The lateral flow sandwich assay device of claim 1, wherein said predetermined concentration is selected such that its predetermined signal intensity can be used to as a reference to indicate the presence of interferants that negatively impact the interaction and binding of analyte and diffusibly bound labeled reagent in said first region such that the absence of signal in both of said reference region and said test region in combination with presence of signal in the control region indicates the likelihood of a false negative result.

17. The lateral flow sandwich assay device of claim 14, wherein said instrument is a reflectance spectrometer.

* * * * *